United States Patent
Oota

(10) Patent No.: US 10,913,818 B2
(45) Date of Patent: Feb. 9, 2021

(54) EPOXY RESIN, EPOXY RESIN COMPOSITION, CURED PRODUCT AND ELECTRICAL OR ELECTRONIC COMPONENT

(71) Applicant: MITSUBISHI CHEMICAL CORPORATION, Tokyo (JP)

(72) Inventor: Kazumasa Oota, Mie (JP)

(73) Assignee: MITSUBISHI CHEMICAL CORPORATION, Tokyo (JP)

(*) Notice: Subject to any disclaimer, the term of this patent is extended or adjusted under 35 U.S.C. 154(b) by 0 days.

(21) Appl. No.: 15/910,707

(22) Filed: Mar. 2, 2018

(65) Prior Publication Data

US 2018/0215862 A1 Aug. 2, 2018

Related U.S. Application Data

(63) Continuation of application No. PCT/JP2016/075727, filed on Sep. 1, 2016.

(30) Foreign Application Priority Data

Sep. 3, 2015 (JP) .................... 2015-173911
Sep. 3, 2015 (JP) .................... 2015-174043

(51) Int. Cl.
| | | |
|---|---|---|
| H01L 23/29 | (2006.01) | |
| C08G 59/24 | (2006.01) | |
| C08L 63/00 | (2006.01) | |
| C09J 163/00 | (2006.01) | |
| C07D 301/28 | (2006.01) | |
| C07D 303/27 | (2006.01) | |
| C07D 303/28 | (2006.01) | |
| C08G 59/06 | (2006.01) | |
| C08G 59/62 | (2006.01) | |
| C08G 59/68 | (2006.01) | |
| C08G 59/40 | (2006.01) | |

(52) U.S. Cl.
CPC ......... *C08G 59/245* (2013.01); *C07D 301/28* (2013.01); *C07D 303/27* (2013.01); *C07D 303/28* (2013.01); *C08G 59/063* (2013.01); *C08G 59/40* (2013.01); *C08G 59/621* (2013.01); *C08G 59/688* (2013.01); *C08L 63/00* (2013.01); *C08L 2203/20* (2013.01); *C08L 2205/025* (2013.01)

(58) Field of Classification Search
None
See application file for complete search history.

(56) References Cited

U.S. PATENT DOCUMENTS

| | | |
|---|---|---|
| 5,141,974 A | 8/1992 | Konishi et al. |
| 5,149,730 A | 9/1992 | Murata et al. |
| 2003/0027942 A1* | 2/2003 | Oota .............. C08F 283/06 525/461 |
| 2018/0215862 A1 | 8/2018 | Oota |

FOREIGN PATENT DOCUMENTS

| | | | |
|---|---|---|---|
| JP | 58-039677 A | 3/1983 | |
| JP | 61-047725 A | 3/1986 | |
| JP | 03-14818 A | 1/1991 | |
| JP | 05-36867 A | 2/1993 | |
| JP | 10-147629 A | 6/1998 | |
| JP | 2000-239346 A | 9/2000 | |
| JP | 2003-41118 A | 2/2003 | |
| JP | 2006257445 A * | 9/2006 | ............ C08G 59/06 |
| JP | 2013-67694 A | 4/2013 | |
| JP | 2017-048387 A | 3/2017 | |
| JP | 2017-048388 A | 3/2017 | |

OTHER PUBLICATIONS

Machine translation of JP-2006257445-A (no date).*
Machine translation of JP-05036867-A (no date).*
"A Survey on Recent Progresses in Epoxy Resins, No. 1", First Edition, *The Japan Society of Epoxy Resin Technology*, Mar. 18, 2009, pp. 8-11.
International Search Report dated Oct. 4, 2016 for the corresponding PCT Application No. PCT/JP2016/075727.
Written Opinion dated Oct. 4, 2016 for the corresponding PCT Application No. PCT/JP2016/075727.
Chinese Office Action dated Aug. 22, 2019 for the corresponding Chinese Patent Application No. 201680051041.0.
Japanese Office Action dated Jan. 28, 2020 for the related Japanese Patent Application No. 2016-171060.
Japanese Office Action dated Jan. 28, 2020 for the related Japanese Patent Application No. 2016-171165.
Taiwanese Office Action dated Apr. 14, 2020 for the corresponding Taiwanese Patent Application No. 105128704.
Chinese Office Action dated Jun. 17, 2020 for the corresponding Chinese Patent Application No. 201680051041.0.
Japanese Office Action dated Sep. 1, 2020 for the corresponding Japanese Patent Application No. 2016-171165.

(Continued)

*Primary Examiner* — Michael J Feely
(74) *Attorney, Agent, or Firm* — Leason Ellis LLP

(57) ABSTRACT

The present invention relates to a tetramethylbiphenol epoxy resin represented by the following formula (1), which is an epoxy resin having excellent solvent solubility, a small hydrolyzable chlorine amount and further an appropriate melt viscosity and being effectively applicable, to a semiconductor sealing material and electrical or electronic components such as laminate sheet:

(1)

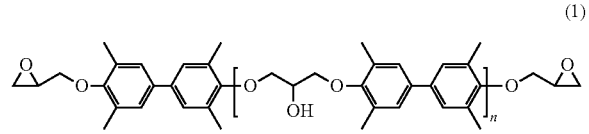

wherein n represents an integer of 0 to 10.

9 Claims, No Drawings

(56) References Cited

OTHER PUBLICATIONS

Chinese Office Action dated Nov. 13, 2020 for the corresponding Chinese Patent Application No. 201680051041.0.

* cited by examiner

EPOXY RESIN, EPOXY RESIN COMPOSITION, CURED PRODUCT AND ELECTRICAL OR ELECTRONIC COMPONENT

TECHNICAL FIELD

The present invention relates to a tetramethylbiphenol epoxy resin having excellent solvent solubility and a small hydrolyzable chlorine amount, an epoxy resin composition containing the epoxy resin and having excellent heat resistance, and a cured product.

The present invention also relates to a tetramethylbiphenol epoxy resin having a high crystallization rate and excellent productivity, an epoxy resin composition containing the epoxy resin and having a low modulus of elasticity in high temperature and excellent heat resistance, and a cured product. The epoxy resin composition of the present invention is useful for electrical or electronic components.

BACKGROUND ART

The epoxy resin generally provides a cured product excellent in mechanical property, heat resistance, electrical property, etc. by curing with various curing agents and therefore, is utilized in wide fields such as adhesive, paint, and electrical or electronic material. Among others, in the field of electrical or electronic materials, a tetramethylbiphenol epoxy resin is often used for the application to a semiconductor sealing material, since a sealing material with a high added value can be provided.

Patent Document 1 describes that a tetramethylbiphenol epoxy resin was produced by reacting 4,4'-bishydroxy-3,3', 5,5'-tetramethylbiphenyl with epichlorohydrin.

Patent Document 2 indicates a tetramethylbiphenol epoxy resin having an epoxy equivalent of 190 g/eq or less and a hydrolyzable chlorine amount of 500 ppm or less and specifically indicates that a tetramethylbiphenol epoxy resin having an epoxy equivalent of 184 g/eq and a hydrolyzable chlorine amount of 290 ppm or having an epoxy equivalent of 182 g/eq and a hydrolyzable chlorine amount of 230 ppm was produced.

Patent Document 3 describes that an epoxy resin having an epoxy equivalent of 188 or 190 and a content of entire organic chlorine of 410 or 340 ppm was obtained by adding a KOH or NaOH/isopropanol solution to a commercially available tetramethylbiphenol epoxy resin ("EPIKOTE YX4000", epoxy equivalent: 186, content of entire organic halogen: 1,180 ppm) in a mixed solvent of isobutyl ketone and dimethyl sulfoxide and reacting it at 70° C. or 60° C.

Patent Document 4 discloses a tetramethylbiphenol epoxy resin having a weight average molecular weight (Mw) of 300 to 800 and a ratio (Mw/Mn) of Mw and number average molecular weight (Mn) of 1.0 to 1.5, with the purpose of enhancing humidity resistance reliability.

Non-Patent Document 1 discloses a practical epoxy resin for electronic materials as well as a biphenyl epoxy resin normally used for a sealing material, where the hydrolyzable chlorine amount of the resins is from 500 to 700 ppm.

BACKGROUND ART LITERATURE

Patent Document

Patent Document 1: JP-A-58-039677
Patent Document 2: JP-A-10-147629
Patent Document 3: JP-A-2000-239346
Patent Document 4: JP-A-5-36867

Non-Patent Document

Non-Patent Document 1: Edited by The Japan Society of Epoxy Resin Technology, "Review Paper, Epoxy Resin, Latest Advancement I", 1st ed., (Japan), The Japan Society of Epoxy Resin Technology, Mar. 18, 2009, pp. 8-11

SUMMARY OF THE INVENTION

Problems to be Solved by the Invention

However, in Patent Document 1, there is no description of number average molecular weight (Mn) and weight average molecular weight (Mw). This epoxy resin is an epoxy resin in which, as illustrated in Comparative Examples 1-4 later, both the number average molecular weight (Mn) and the weight average molecular weight (Mw) are outside the scope of the present invention, and has poor solvent solubility.

In Patent Document 2, there is no description of number average molecular weight (Mn) and weight average molecular weight (Mw). This epoxy resin should be a lower molecular weight resin than the epoxy resin of the present invention, since the amount of chlorine impurity is small and the epoxy ring is closed, although the epoxy equivalent is low.

The tetramethylbiphenol epoxy resin has excellent heat resistance and moisture absorption resistance due to its rigid tetramethylbiphenyl skeleton and since the melt viscosity at 150° C. is low, the resin not only enables high filling of a filler as a semiconductor sealing material but also is effective in preventing wire flowing at the time of molding of a sealing material for a semiconductor. On the other hand, this resin has the following drawbacks.

Namely, in the application to electrical or electronic materials, an epoxy resin is sometimes used as a varnish by dissolving it in a solvent, but the tetramethylbiphenol epoxy resin has poor solvent solubility because of its rigid tetramethylbiphenyl skeleton. Also from the aspect of chlorine content reduction that is required in recent years, the hydrolyzable chlorine amount is not at a sufficient level.

In Patent Document 3, studies were not made on solvent solubility. In addition, the content of entire organic chlorine is not sufficiently reduced. Also in Patent Document 3, there is no description of the number average molecular weight (Mn) and weight average molecular weight (Mw) of the epoxy resin, and the number average molecular weight (Mn) and weight average molecular weight (Mw) of EPIKOTE YX4000 are outside the specified ranges of the present invention.

In Patent Document 4, the epoxy resin is used for a sealing material of a semiconductor device and although the hydrolyzable chlorine amount of the resin is supposed to be preferably 600 ppm or less, a ring-closing reaction is conducted only once in Examples, which infers that the hydrolyzable chlorine remains in a fairly large amount of about thousands of ppm. In addition, as in Non-Patent Document 1, the hydrolyzable chlorine amount of a conventional product is about 500 ppm and therefore, it is not intended in Patent Document 4 to achieve a further smaller hydrolyzable chlorine amount. In other words, a tetramethylbiphenol epoxy resin having a small hydrolyzable chlorine amount and a specific molecular weight is by no means disclosed in Patent Document 4.

An object of the present invention is to provide a tetramethylbiphenol epoxy resin having excellent solvent solubility and a small hydrolyzable chlorine amount, in comparison with conventional products, an epoxy resin composition containing the epoxy resin and having excellent heat resistance, and a cured product thereof.

Another object of the present invention is to provide a tetramethylbiphenol epoxy resin having a high crystallization rate and excellent productivity, in comparison with conventional products, an epoxy resin composition containing the epoxy resin and having a low modulus of elasticity in high temperature and excellent heat resistance, and a cured product thereof.

Still another object of the present invention is to provide electrical or electronic components including the epoxy resin composition.

Means for Solving the Problems

As a result of intensive studies to attain the objects above, the inventors of the present invention have found that those problems can be solved by a tetramethylbiphenol epoxy resin in which at least either the molecular weight or the hydrolyzable chlorine amount is controlled to a specific range, and an epoxy resin composition containing the epoxy resin, and a curing agent. The present invention has been accomplished based on this finding.

The tetramethylbiphenol epoxy resin has not existed in the past, and it is a knowledge found by the inventors of the present invention that the epoxy resin has excellent solvent solubility and provides a cured product having excellent heat resistance.

That is, the gist of the present invention resides in the following [1] to [10].

[1] An epoxy resin represented by the following formula (1), having a number average molecular weight (Mn) of 270 to 460, a weight average molecular weight (Mw) of 370 to 6,080, and a content of hydrolyzable chlorine of 300 ppm or less relative to the epoxy resin.

[Chem. 1]

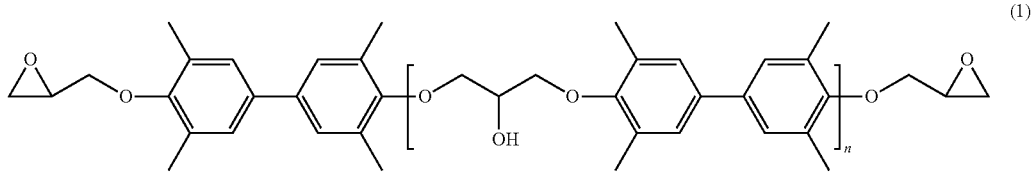

(1)

(In the formula, n represents an integer of 0 to 10.)

[2] The epoxy resin according to [1], wherein the content of hydrolyzable chlorine is 90 ppm or less relative to the epoxy resin.

[3] The epoxy resin according to [1] or [2], wherein the melt viscosity at 150° C. is 3.0 Pa·s or less.

[4] An epoxy resin represented by the following formula (1), having a number average molecular weight (Mn) of 270 to 300.

[Chem. 2]

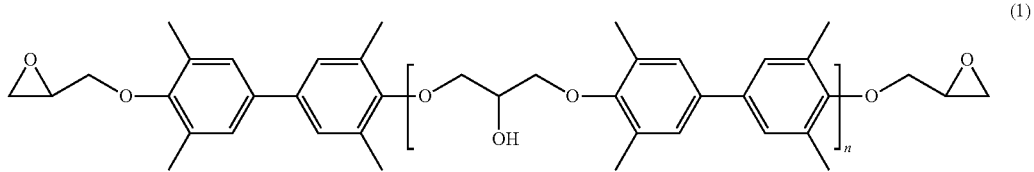

(1)

(In the formula, n represents an integer of 0 to 10.)

[5] An epoxy resin represented by the following formula (1), having a weight average molecular weight (Mw) or 370 to 610.

[Chem. 3]

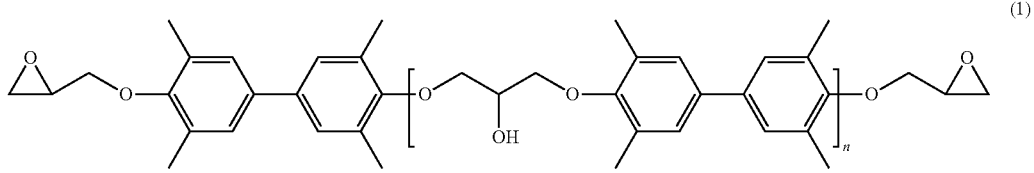

(1)

(In the formula, n represents an integer of 0 to 10.)

[6] An epoxy resin composition containing from 0.1 to 1,000 parts by weight of a curing agent per 100 parts by weight of the epoxy resin according to any one of [1] to [5].

small hydrolyzable chlorine amount and further an appropriate melt viscosity. In addition, the epoxy resin of the present invention has a high crystallization rate and excellent productivity by setting the later-described molecular weight to be in an appropriate range.

[Chem. 4]

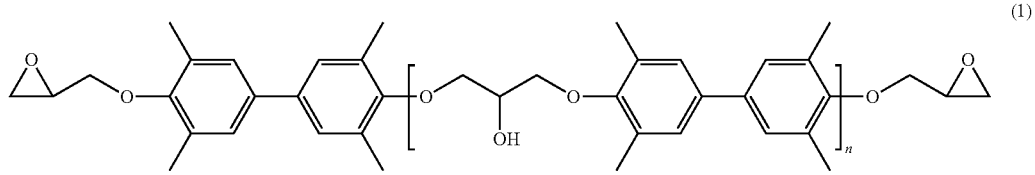

(1)

(In the formula n represents an integer of 0 to 10.)

[7] The epoxy resin composition according to [6], wherein the curing agent is at least one curing agent selected from the group consisting of a phenolic curing agent, an amine curing agent, an acid anhydride curing agent, and an amide curing agent.

[8] The epoxy resin composition according to [6] or [7], further containing an epoxy resin different from the epoxy resin according to any one of [1] to [5].

[9] A cured product obtained by curing the epoxy resin composition according to any one of [6] to [8].

[10] An electric or electronic component obtained by curing the epoxy resin composition according to any one of [6] to [8].

Effect of the Invention

According to the present invention, a tetramethylbiphenol epoxy resin having excellent solvent solubility and a small hydrolyzable chlorine amount, in comparison with conventional products, an epoxy resin composition containing the tetramethylbiphenol epoxy resin and having excellent heat resistance, and a cured product are provided.

According to another embodiment of the present invention, a tetramethylbiphenol epoxy resin having a high crystallization rate and excellent productivity, in comparison with conventional products, an epoxy resin composition containing the tetramethylbiphenol epoxy resin and having a low modulus of elasticity in high temperature and excellent heat resistance, and a cured product are provided.

The epoxy resin composition of the present invention has the above-described effects and therefore, can be effectively applied, among others, to a semiconductor sealing material and electrical or electronic components such as laminate sheet.

MODE FOR CARRYING OUT THE INVENTION

Although the mode for carrying out the present invention is described in detail below, the following description is an example of the embodiment of the present invention, and the present invention is not limited to the following contents as long as its gist is observed. In this connection, the expression "(numerical or physical value) to (numerical or physical value)" as used in the present description is intended to include the numerical or physical values before and after "to".

[Epoxy Resin]

The epoxy resin of the present invention is a tetramethylbiphenol epoxy resin represented by the following formula (1), and this is a resin having excellent solvent solubility, a The epoxy resin of the present invention has excellent solvent solubility and therefore, at the time of using the epoxy resin by dissolving it in a solvent, a larger amount of epoxy resin can be dissolved in the solvent, by which a high degree of freedom in blending and formulation is provided.

In another embodiment described below, the epoxy resin has a high crystallization rate and excellent productivity and therefore, the epoxy resin is produced with high production efficiency and good profitability.

Furthermore, the epoxy resin of the present invention has a small hydrolyzable chlorine amount and therefore, in a cured product thereof, the amount of free chlorine is reduced, so that wiring of electrical or electronic equipment can be prevented from corrosion and a trouble such as insulation failure can be prevented.

In addition, the epoxy resin of the present invention has an appropriate melt viscosity and therefore, is also excellent in handleability.

The number of epoxy groups in the tetramethylbiphenol epoxy resin represented by formula (1) (hereinafter, sometimes referred to as "epoxy resin (1)") is indicated as the epoxy equivalent described below.

In formula (1) representing epoxy resin (1), n is an integer of 0 to 10, and epoxy resin (1) is offered as a mixture of a plurality of compounds where n is different within the range of n=0 to 10.

[Weight Average Molecular Weight (Mw)]

Epoxy resin (1) has preferable Mw of 370 to 6,080 from the viewpoint of obtaining excellent solvent solubility, has more preferably from 370 to 2,675 from the viewpoint of providing a good value for melt viscosity; still more preferably from 445 to 2,675 from the viewpoint of achieving further excellent solvent solubility; and yet still more preferably from 615 to 2,657 from the viewpoint of reducing the content of hydrolyzable chlorine and obtaining excellent electric properties.

Although the mechanism by which the solvent solubility is improved is not clarified, it is considered that when Mw is within the range above, crystallinity is inhibited by an oligomer component represented by formula (1) contained in epoxy resin (1).

In addition, epoxy resin (1) preferably has Mw of 370 to 610 from the viewpoint of reducing the content of hydrolyzable chlorine and obtaining excellent electric properties and a high crystallization rate, has more preferably from 370 to 431 from the viewpoint of providing a good value for melt viscosity; and still more preferably from 391 to 431 from the viewpoint of obtaining a more excellent crystallization rate.

Although the mechanism by which the crystallization rate is improved is not clarified, it is considered that when Mw is within the range above, crystallization is promoted by an oligomer component represented by formula (1) contained in epoxy resin (1).

The weight average molecular weight (Mw) can be measured in terms of polystyrene by gel permeation chromatography.

[Number Average Molecular Weight (Mn)]

Epoxy resin (1) preferably has Mn of 270 to 460 from the viewpoint of obtaining excellent solvent solubility, has more preferably from 270 to 411 from the viewpoint of providing a good value for melt viscosity; still more preferably from 281 to 411 from the viewpoint of achieving further excellent solvent solubility; and yet still more preferably from 304 to 411 from the viewpoint of reducing the content of hydrolyzable chlorine and obtaining excellent electric properties.

Although the mechanism by which the solvent solubility is improved is not clarified, it is considered that when Mn is within the range above, crystallinity is inhibited by an oligomer component represented by formula (1) contained in epoxy resin (1).

Epoxy resin (1) preferably has Mn of 270 to 300 from the viewpoint of reducing the content of hydrolyzable chlorine and obtaining excellent electric properties and a high crystallization rate, has more preferably from 270 to 278 from the viewpoint of providing a good value for melt viscosity; and still more preferably from 271 to 278 from the viewpoint of obtaining a more excellent crystallization rate.

Although the mechanism by which the crystallization rate is improved is not clarified, it is considered that when Mn is within the range above, crystallization is promoted by an oligomer component represented by formula (1) contained in epoxy resin (1).

The number average molecular weight (Mn) can be measured in terms of polystyrene by gel permeation chromatography.

It is known that Mw and Mn are calculated according to the following formulae:

$$Mw = \Sigma(Mi^2 \cdot Ni)/\Sigma(Mi \cdot Ni)$$

$$Mn = \Sigma(Mi \cdot Ni)/\Sigma(Ni)$$

M represents a molecular weight, N represents the number of molecules, Mw is a weighted average using the molecular weight as the weight, and Mn is a simple arithmetic average. In general, a monomer component plays the main part in synthesizing a low molecular epoxy resin, and a large difference is less likely to occur between the values of Mw and Mn, while in an epoxy resin containing a large amount of oligomer component, the difference between Mw and Mn increases.

[Preferable Combination of Mn and Mw]

Epoxy resin (1) preferably has Mw of 370 to 6,080 and Mn of 270 to 460 from the viewpoint of obtaining excellent solvent solubility, more preferably has Mw of 370 to 2,675 and Mn of 270 to 411 from the viewpoint of improving the melt viscosity, still more preferably has Mw of 445 to 2,675 and Mn of 281 to 411 from the viewpoint of obtaining further excellent solvent solubility, and yet still more preferably has Mw of 615 to 2,675 and Mn of 304 to 411 from the viewpoint of reducing the content of hydrolyzable chlorine and obtaining excellent electric properties.

Although the mechanism by which the solvent solubility is improved is not clarified, it is considered that when Mn and Mw are within the ranges above, crystallinity is inhibited by an oligomer component represented by formula (1) contained in epoxy resin (1).

Epoxy resin (1) preferably has Mw of 370 to 610 and Mn of 270 to 300 from the viewpoint of reducing the content of hydrolyzable chlorine and obtaining excellent electric properties and a high crystallization rate, more preferably has Mw of 370 to 431 and Mn of 270 to 278 from the viewpoint of improving the melt viscosity, and still more preferably has Mw of 391 to 431 and Mn of 271 to 278 from the viewpoint of obtaining a more excellent crystallization rate.

Although the mechanism by which the crystallization rate is improved is not clarified, it is considered that when Mn and Mw are within the ranges above, crystallization is promoted by an oligomer component represented by formula (1) contained in epoxy resin (1).

[Epoxy Equivalent]

Epoxy resin (1) preferably has an epoxy equivalent of 195 to 275 g/eq from the viewpoint of obtaining excellent solvent solubility, more preferably has from 195 to 255 g/eq from the viewpoint of providing a good value for melt viscosity, still more preferably has from 200 to 255 g/eq from the viewpoint of obtaining further excellent solvent solubility, and yet still more preferably has from 209 to 255 g/eq from the viewpoint of reducing the content of hydrolyzable chlorine and obtaining excellent electric properties.

Although the mechanism by which the solvent solubility is improved is not clarified, it is considered that when the epoxy equivalent is within the range above, crystallinity is inhibited by an oligomer component represented by formula (1) contained in epoxy resin (1).

Epoxy resin (1) preferably has an epoxy equivalent of 195 to 208 g/eq from the viewpoint of reducing the content of hydrolyzable chlorine and obtaining excellent electric properties and a high crystallization rate, more preferably has from 195 to 199 g/eq from the viewpoint of providing a good value for melt viscosity, and still more preferably has from 196 to 199 g/eq from the viewpoint of obtaining a more excellent crystallization rate.

Although the mechanism by which the crystallization rate is improved is not clarified, it is considered that when the epoxy equivalent is within the range above, crystallization is promoted by an oligomer component represented by formula (1) contained in epoxy resin (1).

The "epoxy equivalent" as used in the present invention is defined as "the mass of epoxy resin containing one equivalent of epoxy group" and can be measured in conformity with JIS K7236.

[Preferable Combination of Mn and Epoxy Equivalent]

Epoxy resin (1) preferably has an epoxy equivalent of 195 to 275 g/eq and Mn of 270 to 460 from the viewpoint of obtaining solvent solubility, more preferably has an epoxy equivalent of 195 to 255 g/eq and Mn of 270 to 411 from the viewpoint of improving the melt viscosity, still more preferably has an epoxy equivalent of 200 to 255 g/eq and Mn of 281 to 411 from the viewpoint of obtaining further excellent solvent solubility, and yet still more preferably has an epoxy equivalent of 209 to 255 g/eq and Mn of 304 to 411 from the viewpoint of reducing the content of hydrolyzable chlorine and obtaining excellent electric properties.

Although the mechanism by which the solvent solubility is improved is not clarified, it is considered that when Mn and epoxy equivalent are within the ranges above, crystallinity is inhibited by an oligomer component represented by formula (1) contained in epoxy resin (1).

Epoxy resin (1) preferably has an epoxy equivalent of 195 to 208 g/eq and Mn of 270 to 300 from the viewpoint of reducing the content of hydrolyzable chlorine and obtaining excellent electric properties and a high crystallization rate, more preferably has an epoxy equivalent of 195 to 199 g/eq and Mn of 270 to 278 from the viewpoint of improving the melt viscosity, and still more preferably has an epoxy equivalent of 196 to 199 g/eq and Mn of 271 to 278 from the viewpoint of obtaining a more excellent crystallization rate.

Although the mechanism by which the crystallization rate is improved is not clarified, it is considered that when Mn and epoxy equivalent are within the ranges above, crystallization is promoted by an oligomer component represented by formula (1) contained in epoxy resin (1).

[Preferable Combination of Mw and Epoxy Equivalent]

Epoxy resin (1) preferably has an epoxy equivalent of 195 to 275 g/eq and Mw of 370 to 6,080 from the viewpoint of obtaining excellent solvent solubility, more preferably has an epoxy equivalent of 195 to 255 g/eq and Mw of 370 to 2,675 from the viewpoint of improving the melt viscosity, still more preferably has an epoxy equivalent of 200 to 255 g/eq and Mw of 445 to 2,675 from the viewpoint of obtaining further excellent solvent solubility, and yet still more preferably has an epoxy equivalent of 209 to 255 g/eq and Mw of 615 to 2,675 from the viewpoint of reducing the content of hydrolyzable chlorine and obtaining excellent electric properties.

Although the mechanism by which the solvent solubility is improved is not clarified, it is considered that when Mw and epoxy equivalent are within the ranges above, crystallinity is inhibited by an oligomer component represented by formula (1) contained in epoxy resin (1).

Epoxy resin (1) preferably has an epoxy equivalent of 195 to 208 g/eq and Mw of 370 to 610 from the viewpoint of reducing the content of hydrolyzable chlorine and obtaining excellent electric properties and a high crystallization rate, more preferably has an epoxy equivalent of 195 to 199 g/eq and Mw of 370 to 431 from the viewpoint of improving the melt viscosity, and still more preferably has an epoxy equivalent of 196 to 199 g/eq and Mw of 391 to 431 from the viewpoint of obtaining a more excellent crystallization rate.

Although the mechanism by which the crystallization rate is improved is not clarified, it is considered that when Mw and epoxy equivalent are within the ranges above, crystallization is promoted by an oligomer component represented by formula (1) contained in epoxy resin (1).

[Preferable Combination of Mn, Mw and Epoxy Equivalent]

Epoxy resin (1) preferably has an epoxy equivalent of 195 to 275 g/eq, Mw of 370 to 6,080 and Mn of 270 to 460 from the viewpoint of obtaining excellent solvent solubility, more preferably has an epoxy equivalent of 195 to 255 g/eq, Mw of 370 to 2,675 and Mn of 270 to 411 from the viewpoint of improving the melt viscosity, still more preferably has an epoxy equivalent of 200 to 255 g/eq, Mw of 445 to 2,675 and Mn of 281 to 411 from the viewpoint of obtaining further excellent solvent solubility, and yet still more preferably has an epoxy equivalent of 209 to 255 g/eq, Mw of 615 to 2,675 and Mn of 304 to 411 from the viewpoint of reducing the content of hydrolyzable chlorine and obtaining excellent electric properties.

Although the mechanism by which the solvent solubility is improved is not clarified, it is considered that when Mn, Mw and epoxy equivalent are within the ranges above, crystallinity is inhibited by an oligomer component represented by formula (1) contained in epoxy resin (1).

Epoxy resin (1) preferably has an epoxy equivalent of 195 to 208 g/eq, Mw of 370 to 610 and Mn of 270 to 300 from the viewpoint of reducing the content of hydrolyzable chlorine and obtaining excellent electric properties and a high crystallization rate, more preferably has an epoxy equivalent of 195 to 199 g/eq, Mw of 370 to 431 and Mn of 270 to 278 from the viewpoint of improving the melt viscosity, and still more preferably has an epoxy equivalent of 196 to 199 g/eq, Mw of 391 to 431 and Mn of 271 to 278 from the viewpoint of obtaining a more excellent crystallization rate.

Although the mechanism by which the crystallization rate is improved by setting Mn, Mw and epoxy equivalent at specific ranges above is not clarified, it is considered that when Mn, Mw and epoxy equivalent are within the ranges above, crystallization is promoted by an oligomer component represented by formula (1) contained in epoxy resin (1).

The epoxy equivalent, Mw and Mn of epoxy resin (1) may be caused to fall in the preferable ranges above by, in the later-described production method of epoxy resin (1), controlling the amount of a strong alkali used, the reaction temperature, or the reaction time, in purifying crude epoxy resin by the reaction of crude epoxy resin with a strong alkali.

In addition, a desired resin can be obtained by confirming each numerical value by a method including sampling over time and analysis with GPC.

[Hydrolyzable Chlorine Amount]

In the epoxy resin (1), the content of hydrolyzable chlorine (hereinafter, sometimes referred to as "hydrolyzable chlorine amount") is preferably 300 ppm or less. When the hydrolyzable chlorine amount is 300 ppm or less, the solvent solubility is improved. Among others, the solubility in a polar solvent is improved.

Here, the "ppm" in the hydrolyzable chlorine amount means ppm by weight.

The solvent is not particularly limited but includes, for example, an aromatic hydrocarbon solvent such as benzene and toluene, and an aliphatic hydrocarbon solvent such as hexane, in addition to the following polar solvent.

The polar solvent is not particularly limited but includes, for example, ketones such as methyl ethyl ketone (MEK), methyl isobutyl ketone (MIBK) and acetone, and alcohols such as methanol and ethanol.

The hydrolyzable chlorine amount is more preferably 200 ppm or less, still more preferably 90 ppm or less.

The hydrolyzable chlorine amount is preferably smaller in view of electrical reliability, etc. of the product obtained and, among others, is preferably 80 ppm or less. The lower limit of the hydrolyzable chlorine amount is 0 ppm, i.e., "below detection limit" in the following measurement of the hydrolyzable chlorine amount, but if the hydrolyzable chlorine amount is excessively reduced, the epoxy equivalent, Mw and Mn can be hardly caused to fall in the preferable ranges above. Hence, the lower limit of the hydrolyzable chlorine amount is usually 10 ppm.

The method for measuring the hydrolyzable chlorine amount includes, for example, a method of dissolving about 0.5 g of epoxy resin in 20 ml of dioxane and after refluxing for 30 minutes with 5 ml of a 1 N KOH/ethanol solution, titrating the solution with a 0.01 N silver nitrate solution, thereby determining the amount.

The hydrolyzable chlorine amount in epoxy resin (1) may be reduced by, in the later-described production method of epoxy resin (1), purifying crude epoxy resin by the reaction of crude epoxy resin with a strong alkali.

[Melt Viscosity]

Epoxy resin (1) preferably has a melt viscosity at 150° C. of 3.0 Pa·s or less in view of handleability, and from the viewpoint of more improving the handleability, the melt viscosity is more preferably 0.001 Pa·s or more and 1.4 Pa·s or less.

The "melt viscosity" as used in the present invention is a viscosity determined by melting the epoxy resin on a hot plate adjusted to 150° C. of a cone-plate viscometer (manufactured by Tokai Yagami Co., Ltd.) and measuring the viscosity at a rotational speed of 750 rpm.

The melt viscosity of epoxy resin (1) may be caused to fall in the preferable range above by, in the later-described production method of epoxy resin (1), for example, in the case of a production method by a one-step process, controlling the use amount of epichlorohydrin relative to the raw material polyvalent hydroxy compound. The melt viscosity can be lowered by increasing the amount of epichlorohydrin, and the melt viscosity can be raised by decreasing the amount.

[Production Method of Epoxy Resin (1)]

The epoxy resin (1) of the present invention having Mw, Mn and epoxy equivalent in the preferable ranges above and satisfying the above-described preferable hydrolyzable chlorine amount and melt viscosity can be produced in a usual manner by producing a tetramethylbiphenol epoxy resin (hereinafter, sometimes referred to as "crude epoxy resin") and then purifying the crude epoxy resin by the reaction with a strong alkali.

[Production Method of Crude Epoxy Resin]

The production method of a crude epoxy resin is not particularly limited but includes, for example, the below-described production method by a one-step process.

<Production Method by One-Step Process>

In the production method by a one-step process, the crude epoxy resin is produced by reacting 4,4'-bishydroxy-3,3',5,5'-tetramethylbiphenyl (hereinafter, sometimes referred to as "tetramethylbiphenol (2)") represented by the following formula with epichlorohydrin.

[Chem. 5]

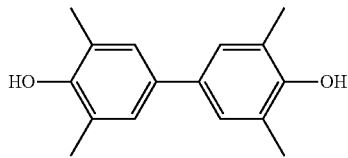

(2)

In this connection, although in the case of producing the crude epoxy resin by a one-step process, at least tetramethylbiphenol (2) and epichlorohydrin are used as the raw material, the crude epoxy resin may be produced as a mixture of epoxy resin (1) and other epoxy resin by using, in combination, a polyvalent hydroxy compound other than tetramethylbiphenol (2) (hereinafter, the compound is sometimes referred to as "other polyvalent hydroxy compound").

However, from the viewpoint of increasing the effects of the present invention, the proportion of tetramethylbiphenol (2) is preferably 30 mol % or more, more preferably 50 mol % or more, still more preferably 80 mol % or more, and yet still more preferably 100 mol %, relative to the total amount of polyvalent hydroxy compounds used as the raw material. The upper limit thereof is 100 mol %.

The "polyvalent hydroxy compound" as used in the present invention is a generic term of a divalent or higher-valent phenol compound and a dihydric or higher-hydric alcohol.

Examples of the other polyhydric compound include various polyvalent phenols (excluding tetramethylbiphenol (2)) such as bisphenol A, bisphenol F, bisphenol S, bisphenol AD, bisphenol AF, hydroquinone, resorcin, methyl resorcin, biphenol, dihydroxynaphthalene, dihydroxydiphenyl ether, thiodiphenols, phenol novolak resin, cresol novolak resin, phenol aralkyl resin, biphenyl aralkyl resin, naphthol aralkyl resin, terpene phenolic resin, dicyclopentadiene phenolic resin, bisphenol A novolak resin, naphthol novolak resin, brominated bisphenol A and brominated phenol novolak resin; polyvalent phenolic resins obtained by a condensation reaction of various phenols with various aldehydes such as benzaldehyde, hydroxybenzaldehyde, crotonaldehyde and glyoxal; polyvalent phenolic resins obtained by a condensation reaction of a xylene resin with phenols; various phenolic resins such as co-condensed resin of heavy oil or pitches with phenols and formaldehydes; chain aliphatic diols such as ethylene glycol, trimethylene glycol, propylene glycol, 1,3-butanediol, 1,4-butanediol, 1,3-pentanediol, 1,4-pentanediol, 1,5-pentanediol and 1,6-hexanediol; cyclic aliphatic diols such as cyclohexanediol and cyclodecanediol; and polyalkylene ether glycols such as polyethylene ether glycol, polyoxytetramethylene ether glycol and polypropylene ether glycol.

Among these, preferred are, for example, a phenol novolak resin, a phenol aralkyl resin, a polyvalent phenol resin obtained by a condensation reaction of phenol with hydroxybenzaldehyde, a biphenyl aralkyl resin, a naphthol aralkyl resin, chain aliphatic diols such as ethylene glycol, trimethylene glycol, propylene glycol, 1,3-butanediol, 1,4-butanediol, 1,3-pentanediol, 1,4-pentanediol, 1,5-pentanediol and 1,6-hexanediol, cyclic aliphatic diols such as cyclohexanediol and cyclodecanediol, and polyalkylene ether glycols such as polyethylene ether glycol, polyoxytrimethylene ether glycol and polypropylene ether glycol.

Tetramethylbiphenol (2) used as the raw material and other polyvalent hydroxy compound used, if desired, are dissolved in epichlorohydrin of an amount corresponding to usually 0.8 to 20 equivalents, preferably from 0.9 to 15 equivalents, more preferably from 1.0 to 10 equivalents, per equivalent of the hydroxyl group in the entire polyvalent hydroxy compound, i.e., the total of these polyvalent hydroxy compounds, to make a uniform solution. The amount of epichlorohydrin is preferably not less than the lower limit above for the reason that a molecular weight-increasing reaction is easily controlled and the obtained epoxy resin can have an appropriate melt viscosity. On the other hand, the amount of epichlorohydrin is preferably not more than the upper limit above, since the production efficiency tends to be enhanced.

Subsequently, with stirring the solution, an alkali metal hydroxide in an amount corresponding to usually from 0.5 to 2.0 equivalents, preferably from 0.7 to 1.8 equivalents, more preferably from 0.9 to 1.6 equivalents, per equivalent of the hydroxyl group in the entire polyhydric hydroxy compound as the raw material is added in the form of a solid or an aqueous solution and reacted. The amount of an alkali metal hydroxide is preferably not less than the lower limit above for the reason that an unreacted hydroxyl group is less likely to react with the produced epoxy resin, facilitating control of a molecular weight-increasing reaction. In addition, the amount of an alkali metal hydroxide is preferably not more than the upper limit value above, since an impurity from a side reaction is less likely to be produced. The alkali metal hydroxide used here is usually sodium hydroxide or potassium hydroxide.

The reaction above can be performed under normal pressure or reduced pressure, and the reaction temperature is preferably from 40 to 150° C., more preferably from 60 to 100° C., and still more preferably from 80 to 100° C. A reaction temperature not less than the lower limit above is preferred, since the reaction is readily allowed to proceed and at the same time, the reaction is easily controlled. In addition, a reaction temperature not more than the upper limit above is advantageous in that a side reaction is less likely to proceed and it is easy to reduce, among others, a chlorine impurity.

The reaction is performed with dehydrating water by a method of azeotroping the reaction solution by keeping a predetermined temperature as needed, subjecting a condensate obtained by cooling volatilized vapor to oil/water separation, and returning oil after removal of water to the reaction system. The alkali metal hydroxide is added intermittently or continuously little by little preferably over 0.1 to 8 hours, more preferably over 0.1 to 7 hours, still more preferably over 0.5 to 6 hours, so as to suppress a rapid reaction. The time spent during adding the alkali metal hydroxide is preferably not less than the lower limit above, since the reaction can be prevented from rapidly proceeding and control of the reaction temperature is facilitated. The addition time is preferably not more than the upper limit above for the reason that a chlorine impurity is less likely to be produced, and this is also preferable in view of profitability. The total reaction time is usually from 1 to 15 hours. After the completion of reaction, an insoluble byproduct salt is removed by filtration or removed by water washing, and unreacted epichlorohydrin is then removed by distillation under reduced pressure, as a result, the target crude epoxy resin can be obtained.

In addition, in the reaction above, a catalyst, for example, a quaternary ammonium salt such as tetramethylammonium chloride and tetraethylammonium bromide, a tertiary amine such as benzyldimethylamine and 2,4,6-tris(dimethylaminomethyl)phenol, imidazoles such as 2-ethyl-4-methylimidazole and 2-phenylimidazole, a phosphonium salt such as ethyltriphenylphosphonium iodide, and phosphines such as triphenylphosphine, may also be used.

Furthermore, in the reaction above, an inert organic solvent, for example, alcohols such as ethanol and isopropanol, ketones such as acetone and methyl ethyl ketone, ethers such as dioxane and ethylene glycol dimethyl ether, glycol ethers such as methoxypropanol, and an aprotic polar solvent such as dimethylsulfoxide and dimethylformamide, may also be used.

[Purification of Crude Epoxy Resin]

In the present invention, the crude epoxy resin produced as above is purified by reacting it with a strong alkali, whereby the solvent solubility is improved or the hydrolyzable chlorine amount is reduced.

In addition, by this reaction with a strong alkali, Mw and Mn as well as the epoxy equivalent can be adjusted to preferable ranges specified in the present invention.

More specifically, for example, Mw can be made high by increasing the temperature, the resin content relative to solvent, or the alkali amount, and conversely, Mw can be made low by decreasing the temperature, the resin content relative to solvent, or the alkali amount. In addition, Mn can be made high by increasing the temperature, the resin content relative to solvent, or the alkali amount, and conversely, Mn can be made low by decreasing the temperature, the resin content relative to solvent, or the alkali amount. Furthermore, the epoxy equivalent can be made high by increasing the temperature, the resin content relative to solvent, or the alkali amount, and conversely, the epoxy equivalent can be made low by decreasing the temperature, the resin content relative to solvent, or the alkali amount.

With respect to the melt viscosity, the melt viscosity can be made high by increasing the temperature, the resin content relative to solvent, or the alkali amount, and conversely, the melt viscosity can be made low by decreasing the temperature, the resin content relative to solvent, or the alkali amount.

With respect to the content of hydrolyzable chlorine, the content of hydrolyzable chlorine can be made small by increasing the temperature, the resin content relative to solvent, or the alkali amount, and conversely, the content of hydrolyzable chlorine can be made large by decreasing the temperature, the resin content relative to solvent, or the alkali amount.

Although detailed conditions for producing the epoxy resin of the present invention are described below, since the reaction time becomes long or short depending on the conditions, a desired epoxy resin can be obtained by appropriately taking a sample, and analyzing Mw and Mn as well as the epoxy equivalent as described above.

In the reaction of the crude epoxy resin with a strong alkali, an organic solvent for dissolving the epoxy resin may be used. Although the organic solvent used for the reaction is not particularly limited, in view of purification efficiency, handleability, workability, etc., a mixed solvent of an aprotic polar solvent and an inert organic solvent except for an aprotic polar solvent is preferred.

The aprotic polar solvent includes, for example, dimethylsulfoxide, dimethylsulfoxide, dimethylsulfone, sulfolane, dimethylformamide, dimethylacetamide, and hexamethylphosphoramide. One of these may be used alone, or two or more thereof may be mixed and used. Among these aprotic polar solvents, dimethylsulfoxide is preferred because of its availability and excellent effect.

The organic solvent used together with the aprotic polar solvent includes, for example, an aromatic hydrocarbon solvent such as benzene, toluene and xylene, a ketone solvent such as methyl ethyl ketone, methyl isobutyl ketone and cyclohexanone, and ethers such as dioxane and ethylene glycol dimethyl ether. In view of effects or ease of post-treatment, an aromatic hydrocarbon solvent or a ketone solvent is preferred, and toluene, xylene or methyl isobutyl ketone is more preferred. One of these may be used alone, or two or more thereof may be mixed and used.

The aprotic polar solvent and other organic solvent are preferably used such that the proportion of the aprotic polar solvent becomes from 3 to 20 wt % relative to the total of these solvents.

The amount of the organic solvent is usually such an amount that the concentration of the crude epoxy resin becomes from 3 to 70 wt %, preferably from 5 to 50 wt %, and more preferably from 10 to 40 wt %.

As the strong alkali, a solid or solution of an alkali metal hydroxide can be used, and the alkali metal hydroxide includes potassium hydroxide, sodium hydroxide, etc.

The crude epoxy resin obtained by epoxidation of tetramethylbiphenol (2) contains a 1,2-chlorohydrin form or a 1,3-chlorohydrin form, and at reaction with a strong alkali, dechlorination of a 1,2-chlorohydrin form proceeds, thereby effecting ring opening and epoxidation. When the reaction of crude epoxy resin with a strong alkali is conducted one or more times, preferably two or more times, more preferably three or more times, the 1,2-chlorohydrin form decreases and in turn, the hydrolyzable chlorine amount is reduced.

In the case of using potassium hydroxide as the alkali metal oxide, a chlorine atom, for example, in 1,2-chlorohydrin form, 1,3-chlorohydrin form or a compound formed by the reaction thereof with epichlorohydrin can be converted into a hydroxyl group and not only the hydrolyzable chlorine amount can be further reduced but also the solubility in a polar solvent can be enhanced due to introduction of a hydroxyl group.

The alkali metal hydroxide may be used by dissolving it in an organic solvent or water. The amount of the alkali metal hydroxide used is, in terms of solid content of the alkali metal hydroxide, preferably 0.2 parts by weight or more and 1.1 parts by weight or less, per 100 parts by weight of the crude epoxy resin. When the amount of the alkali metal hydroxide used is in this range, Mn and Mw as well as the epoxy equivalent of epoxy resin (1) can be easily adjusted to fall in the preferable ranges above.

The reaction temperature is preferably from 30 to 120° C., and more preferably from 40 to 110° C., and the reaction time is preferably from 0.1 to 15 hours, and more preferably from 0.3 to 12 hours.

After the reaction, an excess alkali metal hydroxide or a byproduct salt is removed by water washing or other methods, as a result, epoxy resin (1) of the present invention obtained.

The method for controlling the molecular weight of the epoxy resin of the present invention includes a method of taking a sample over time, analyzing it with GPC, and controlling the molecular weight based on the results.

The epoxy resin of the present invention can be produced by effecting epoxidation with epichlorohydrin, and performing the above-described treatment.

[Epoxy Resin Composition]

The epoxy resin composition of the present invention contains at least the above-described epoxy resin (1) of the present invention and a curing agent. In the epoxy resin composition of the present invention, an epoxy resin other than epoxy resin (1) of the present invention (hereinafter, sometimes simply referred to as "other epoxy resin"), a curing accelerator, an inorganic filler, a coupling agent, etc. may be appropriately blended.

The epoxy resin composition of the present invention containing epoxy resin (1) of the present invention having excellent solvent solubility and a small hydrolyzable chlorine amount is excellent in the cured product properties such as heat resistance and moisture absorption resistance and provides a cured product sufficiently satisfying various physical properties required for a variety of applications.

In addition, the epoxy resin composition of the present invention containing epoxy resin (1) of the present invention having a high crystallization rate and a small hydrolyzable chlorine amount is excellent in the cured product properties such as heat resistance and moisture absorption resistance and provides a cured product sufficiently satisfying various physical properties required for a variety of applications.

More specifically, epoxy resin (1) has a rigid tetramethylbiphenyl skeleton and therefore, provides a cured product excellent in heat resistance and moreover in moisture absorption resistance. When the epoxy resin composition and cured product have excellent heat resistance, in the case of use as a semiconductor sealing material, etc., a product with excellent reliability can be realized by ensuring generation of little thermal stress in the resin sealed and insusceptibility to damage to passivation or chip or failure such as sliding and package cracking of aluminum wiring.

[Curing Agent]

The curing agent as used in the present invention indicates a substance contributing to a crosslinking reaction between epoxy groups and/or a chain extension reaction of the epoxy resin. In this connection, in the present invention, even a substance usually called a "curing accelerator" is regarded as a curing agent if it contributes to a crosslinking reaction between epoxy groups and/or a chain extension reaction of the epoxy resin.

In the epoxy resin composition of the present invention, the content of the curing agent is, as the solid content, preferably from 0.1 to 1,000 parts by weight per 100 parts by weight of the entire epoxy resin component. In addition, the content is more preferably 500 parts by weight or less, and still more preferably 300 parts by weight or less. The "solid content" as used in the present invention means components excluding the solvent and encompasses not only a solid epoxy resin but also a semi-solid or viscous liquid material. In addition, the "entire epoxy resin component" corresponds to the amount of the epoxy resin contained in the epoxy resin composition of the present invention and corresponds to the amount of epoxy resin (1) in the case where the epoxy resin composition of the present invention contains only epoxy resin (1), or corresponds to the total of epoxy resin (1) and other epoxy resin in the case of containing epoxy resin (1) and other epoxy resin.

The curing agent is not particularly limited, and all of those known in general as an epoxy resin-curing agent can be used. Examples thereof include a phenolic curing agent, an amine curing agent such as aliphatic amine, polyether amine, alicyclic amine and aromatic amine, an acid anhydride curing agent, an amide curing agent, tertiary amine, and imidazoles.

Among these, a phenolic curing agent is preferably contained as the curing agent, since the epoxy resin composition of the present invention can be excellent in heat resistance, stress resistance, moisture absorption resistance, flame retardancy, etc. by containing a phenolic curing agent. In addition, in view of heat resistance, etc., it is preferable to contain an acid anhydride curing agent or an amide curing agent. Furthermore, use of imidazoles is also preferred from the viewpoint of allowing the curing reaction to sufficiently proceed and enhancing the heat resistance.

As the curing agent, one kind may be used alone, or two or more kinds may be used in combination. In the case of using two or more kinds of curing agents in combination, these may be previously mixed to prepare a mixed curing agent and then used, or respective components of the curing agent may be separately added at the time of mixing respective components of the epoxy resin composition and mixed simultaneously.

<Phenolic Curing Agent>

Specific examples of the phenolic curing agent include various polyvalent phenols such as bisphenol A, bisphenol F, bisphenol S, bisphenol AD, hydroquinone, resorcin, methylresorcin, biphenol, tetramethylbiphenol, dihydroxynaphthalene, dihydroxydiphenyl ether, thiodiphenols, phenol novolak resin, cresol novolak resin, phenol aralkyl resin, biphenyl aralkyl resin, naphthol aralkyl resin, terpene phenol resin, dicyclopentadiene phenol resin, bisphenol A novolak resin, trisphenolmethane-type resin, naphthol novolak resin, brominated bisphenol A and brominated phenol novolak resin; polyvalent phenol resins obtained by a condensation reaction of various phenols with various aldehydes such as benzaldehyde, hydroxybenzaldehyde, crotonaldehyde and glyoxal; polyvalent phenol resins obtained by a condensation reaction of a xylene resin with phenols; a co-condensed resin of heavy oil or pitches with phenols and formaldehydes; and various phenol resins such as phenol.benzaldehyde.xylylene dimethoxide polycondensate, phenol.benzaldehyde.xylylene dihalide polycondensate, phenol.benzaldehyde.4,4'-dimethoxide biphenyl polycondensate and phenol.benzaldehyde.4,4'-dihalide biphenyl polycondensate.

Only one of these phenolic curing agents may be used, or two or more thereof may be combined and used in any combination in an arbitrary blending ratio.

Among these phenolic curing agents, in view of heat resistance, curability, etc. after curing of the composition, a phenol novolak resin (for example, a compound represented by the following formula (3)), a phenol aralkyl resin (for example, a compound represented by the following formula (4)), a biphenyl aralkyl resin (for example, a compound represented by the following formula (5)), a naphthol novolak resin (for example, a compound represented by the following formula (6)), a naphthol aralkyl resin (for example, a compound represented by the following formula (7)), a trisphenolmethane-type resin (for example, a compound represented by the following formula (8)), a phenol.benzaldehyde.xylylene dimethoxide polycondensate (for example, a compound represented by the following formula (9)), a phenol.benzaldehyde.xylylene dihalide polycondensate (for example, a compound represented by the following formula (9)), a phenol.benzaldehyde.4,4'-dimethoxide biphenyl polycondensate (for example, a compound represented by the following formula (10)), a phenol.benzaldehyde.4,4'-dihalide biphenyl polycondensate (for example, a compound represented by the following formula (10)), and the like are preferred. In particular, a phenol novolak resin (for example, a compound represented by the following formula (3)), a phenol aralkyl resin (for example, a compound represented by the following formula (4)), a biphenyl aralkyl resin (for example, a compound represented by the following formula (5)), a phenol.benzaldehyde.xylylene dimethoxide polycondensate (for example, a compound represented by the following formula (9)), a phenol.benzaldehyde.xylylene dihalide polycondensate (for example, a compound represented by the following formula (9)), a phenol.benzaldehyde.4,4'-dimethoxide biphenyl polycondensate (for example, a compound represented by the following formula (10)), and a phenol.benzaldehyde.4,4'-dihalide biphenyl polycondensate (for example, a compound represented by the following formula (10)) are preferred.

[Chem. 6]

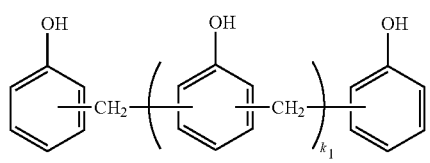

(3)

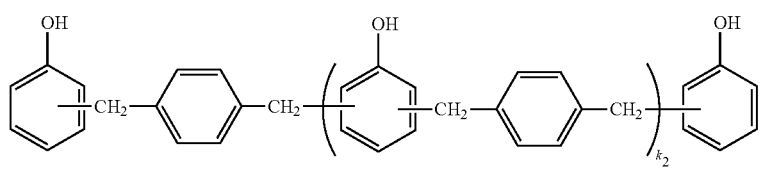

(4)

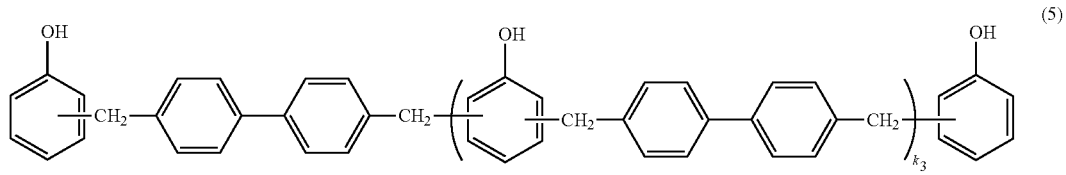

(5)

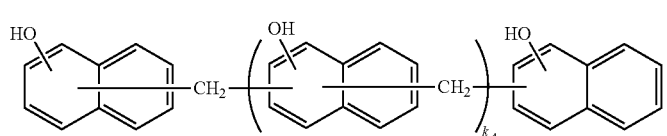

(6)

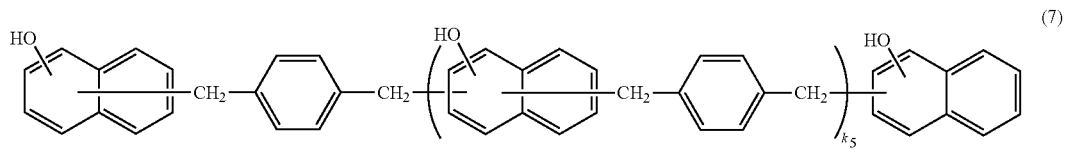

(7)

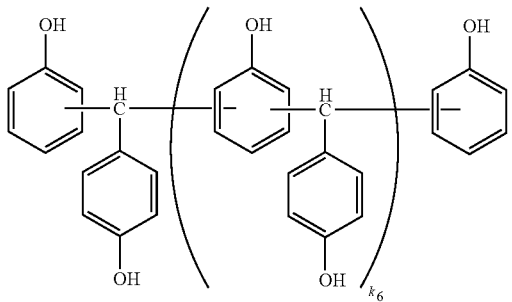

(8)

(in the formulae (3) to (8), each of $k_1$ to $k_6$ represents an integer of 0 or more);

[Chem. 7]

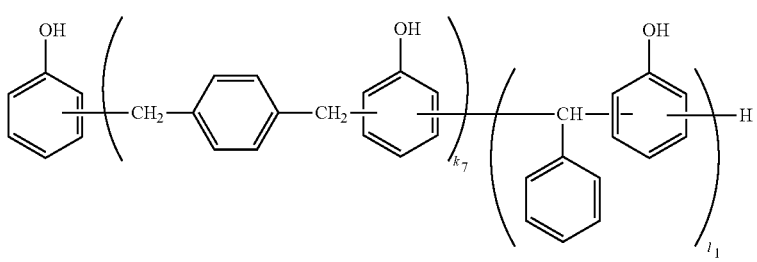

(9)

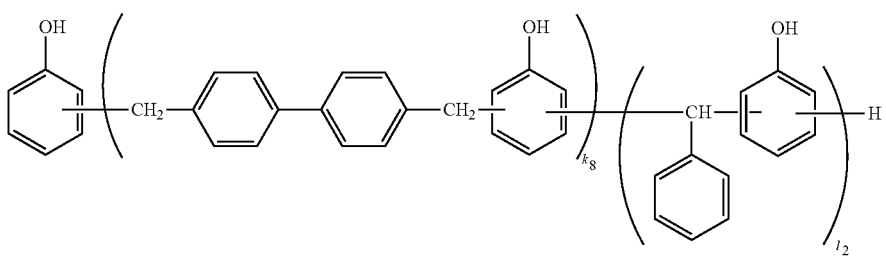

(10)

(in the formulae (9) and (10), each of $k_7$, $k_8$, $l_1$ and $l_2$ represents an integer of 1 or more).

The blending amount of the phenolic curing agent is preferably from 0.1 to 1,000 parts by weight, more preferably 500 parts by weight or less, still more preferably 300 parts by weight or less, yet still more preferably 100 parts by weight or less, per 100 parts by weight of the entire epoxy resin component in the epoxy resin composition.

<Amine Curing Agent>

Examples of the amine curing agent (excluding tertiary amine) include aliphatic amines, polyether amines, alicyclic amines, and aromatic amines.

Examples of the aliphatic amines include ethylenediamine, 1,3-diaminopropane, 1,4-diaminopropane, hexamethylenediamine, 2,5-dimethylhexamethylenediamine, trimethylhexamethylenediamine, diethylenetriamine, iminobispropylamine, bis(hexamethylene)triamine, triethylenetetramine, tetraethylenepentamine, pentaethylenehexamine, N-hydroxyethylethylenediamine, and tetra(hydroxyethyl)ethylenediamine.

Examples of the polyether amines include triethylene glycol diamine, tetraethylene glycol diamine, diethylene glycol bis(propylamine), polyoxypropylenediamine, and polyoxypropylenetriamines.

Examples of the alicyclic amines include isophorone diamine, methacene diamine, N-aminoethylpiperazine, bis(4-amino-3-methyldicyclohexyl)methane, bis(aminomethyl)cyclohexane, 3,9-bis(3-aminopropyl)-2,4,8,10-tetraoxaspiro(5,5)undecane, and norbornene diamine.

Examples of the aromatic amines include tetrachloro-p-xylenediamine, m-xylenediamine, p-xylenediamine, m-phenylenediamine, o-phenylenediamine, p-phenylenediamine, 2,4-diaminoanisole, 2,4-toluenediamine, 2,4-diaminodiphenylmethane, 4,4'-diaminodiphenylmethane, 4,4'-diamino-1,2-diphenylethane, 2,4-diaminodiphenylsulfone, 4,4'-diaminodiphenylsulfone, m-aminophenol, m-aminobenzylamine, benzyldimethylamine, 2-(dimethylaminomethyl)phenol, triethanolamine, methylbenzylamine, α-(m-aminophenyl)ethylamine, α-(p-aminophenyl)ethylamine, diaminodiethyldimethyldiphenylmethane, and α,α'-bis(4-aminophenyl)-p-diisopropylbenzene.

Only one of these amine curing agents may be used, or two or more thereof may be combined and used in any combination in an arbitrary blending ratio.

The amine curing agent above is preferably used in an amount ranging from 0.8 to 1.5 in terms of equivalent ratio of the functional group in the curing agent to the epoxy group in the entire epoxy resin components contained in the epoxy resin composition. The amount within this range is preferred, since an unreacted epoxy group or a functional group of the curing agent is less likely to remain.

Examples of the tertiary amine include 1,8-diazabicyclo(5,4,0)undecene-7, triethylenediamine, benzyldimethylamine, triethanolamine, dimethylaminoethanol, and tris(dimethylaminomethyl)phenol.

Only one of these tertiary amines may be used, or two or more thereof may be combined and used in any combination in an arbitrary blending ratio.

The tertiary amine above is preferably used in an amount ranging from 0.8 to 1.5 in terms of equivalent ratio of the functional group in the curing agent to the epoxy group in the entire epoxy resin components contained in the epoxy resin composition. The amount within this range is preferred, since an unreacted epoxy group or a functional group of the curing agent is less likely to remain.

<Acid Anhydride Curing Agent>

The acid anhydride curing agent includes an acid anhydride, a modified acid anhydride, etc.

The acid anhydride includes, for example, phthalic anhydride, trimellitic anhydride, pyromellitic anhydride, benzophenonetetracarboxylic anhydride, dodecenylsuccinic anhydride, polyadipic anhydride, polyazelaic anhydride, polysebacic anhydride, poly(ethyloctadecane diacid) anhydride, poly(phenylhexadecane diacid) anhydride, tetrahydrophthalic anhydride, methyltetrahydrophthalic anhydride, methylhexahydrophthalic anhydride, hexahydrophthalic anhydride, methylhimic anhydride, trialkyltetrahydrophthalic anhydride, methylcyclohexenedicarboxylic anhydride, methylcyclohexenetetracarboxylic anhydride, ethylene glycol bistrimellitate dianhydride, HET anhydride, nadic anhydride, methyl nadic anhydride, 5-(2,5-dioxotetrahydro-3-furanyl)-3-methyl-3-cyclohexane-1,2-dicarboxylic anhydride, 3,4-dicarboxy-1,2,3,4-tetrahydro-1-naphthalenesuccinic dianhydride, and 1-methyl-dicarboxy-1,2,3,4-tetrahydro-1-naphthalenesuccinic dianhydride.

The modified acid anhydride includes, for example, those obtained by modifying the above-described acid anhydrides with a glycol. Examples of the glycol which can be used for the modification include alkylene glycols such as ethylene glycol, propylene glycol and neopentyl glycol, and polyether glycols such as polyethylene glycol, polypropylene glycol and polytetramethylene ether glycol. Furthermore, a copolymerized polyether glycol of two or more kinds of these glycols and/or polyether glycols can also be used.

In the modified acid anhydride, the acid anhydride is preferably modified with 0.4 mol or less of glycol per 1 mol. When the modification amount is not more than the upper limit value above, the viscosity of the epoxy resin composition does not become excessively high, and it is likely that the workability is improved and a favorable curing reaction rate with the epoxy resin is realized.

Only one of these acid anhydride curing agents may be used, or two or more thereof may be combined and used in any combination in an arbitrary blending ratio.

In the case of using an acid anhydride curing agent, the acid anhydride curing agent is preferably used in an amount ranging from 0.8 to 1.5 in terms of equivalent ratio of the functional group in the curing agent to the epoxy group in the entire epoxy resin components contained in the epoxy resin composition. The amount within this range is preferred, since an unreacted epoxy group or a functional group of the curing agent is less likely to remain.

<Amide Curing Agent>

The amide curing agent includes dicyandiamide, a derivative thereof, a polyamide resin, etc.

As the amide curing agent, only one kind may be used, or two or more kinds may be used in any combination in an arbitrary blending ratio.

In the case of using an amide curing agent, the amide curing agent is preferably used to account for 0.1 to 20 wt % relative to the total of the entire epoxy resin composition and the amide curing agent in the epoxy resin composition.

<Imidazoles>

Examples of the imidazoles include 2-phenylimidazole, 2-ethyl-4(5)-methylimidazole, 2-phenyl-4-methylimidazole, 1-benzyl-2-methylimidazole, 1-benzyl-2-phenylimidazole, 1-cyanoethyl-2-undecylimidazole, 1-cyano-2-phenylimidazole, 1-cyanoethyl-2-undecylimidazole trimellitate, 1-cyanoethyl-2-phenylimidazolium trimellitate, 2,4-diamino-6-[2'-methylimidazolyl-(1')]-ethyl-s-triazine, 2,4-diamino-6-[2'-ethyl-4'-methylimidazolyl-(1')]-ethyl-s-triazine, a 2,4-diamino-6-[2'-methylimidazolyl-(1')]-ethyl-s-triazine isocyanuric acid adduct, a 2-phenylimidazole isocyanuric acid adduct, 2-phenyl-4,5-dihydroxymethylimidazole, 2-phenyl-4-methyl-5-hydroxymethylimidazole, and an adduct of epoxy resin to the imidazoles above. In this connection, the imidazoles have a catalytic ability and therefore, may be generally classified into a curing accelerator but are classified into a curing agent in the present invention.

Only one of these imidazoles may be used, or two or more thereof may be mixed and used in any combination in an arbitrary ratio.

In the case of using imidazoles, the imidazoles are preferably used to account for 0.1 to 20 wt % relative to the total of the entire epoxy resin components and the imidazoles in the epoxy resin composition.

<Other Curing Agents>

In the epoxy resin composition of the present invention, a curing agent other than the above-described curing agents can be used. The other curing agent that can be used in the epoxy resin composition of the present invention is not particularly limited, and all of those known in general as a curing agent for epoxy resins can be used. Only one of these other curing agents may be used, or two or more thereof may be used in combination.

[Other Epoxy Resin]

The epoxy resin composition of the present invention may further contain other epoxy resin, in addition to epoxy resin (1). By incorporating the other epoxy resin, the heat resistance, stress resistance, moisture absorption resistance, flame retardancy, etc. of the epoxy resin composition of the present invention can be enhanced.

As the other epoxy resin that can be used in the epoxy resin composition of the present invention, all epoxy resins except for epoxy resin (1) are appropriate, but specific examples thereof include a bisphenol A-type epoxy resin, a trisphenolmethane-type epoxy resin, an anthracene-type epoxy resin, a phenol-modified xylene resin-type epoxy resin, a bisphenol cyclododecyl-type epoxy resin, a bisphenol diisopropylidene resorcin-type epoxy resin, a bisphenol F-type epoxy resin, a bisphenol AD-type epoxy resin, a hydroquinone-type epoxy resin, a methylhydroquinone-type epoxy resin, a dibutylhydroquinone-type epoxy resin, a resorcin-type epoxy resin, a methylresorcin-type epoxy resin, a biphenol-type epoxy resin, a tetramethylbiphenol-type epoxy resin except for epoxy resin (1), a tetramethylbiphenol F-type epoxy resin, a dihydroxydiphenyl ether-type epoxy resin, an epoxy resin derived from thiodiphenols, a dihydroxynaphthalene-type epoxy resin, a dihydroxyanthracene-type epoxy resin, a dihydroxydihydroanthracene-type epoxy resin, a dicyclopentadiene-type epoxy resin, an epoxy resin derived from dihydroxystilbenes, a phenol novolak-type epoxy resin, a cresol novolak-type epoxy resin, a bisphenol A novolak-type epoxy resin, a naphthol novolak-type epoxy resin, a phenol aralkyl-type epoxy resin, a naphthol aralkyl-type epoxy resin, a biphenyl aralkyl-type epoxy resin, a terpene phenol-type epoxy resin, a dicyclopentadiene phenol-type epoxy resin, an epoxy resin derived from a phenol.hydroxybenzaldehyde condensate, an epoxy resin derived from a phenol.crotonaldehyde condensate, an epoxy resin derived from a phenol.glyoxal condensate, an epoxy resin derived from a co-condensed resin of heavy oil or pitches with phenols and formaldehydes, an epoxy resin derived from diaminodiphenylmethane, an epoxy resin derived from aminophenol, an epoxy resin derived from xylenediamine, an epoxy resin derived from a methylhexahydrophthalic acid, and an epoxy resin derived from a dimer acid. Only one of these may be used, or two or more thereof may be used in any combination in an arbitrary blending ratio.

Among these epoxy resins, in view of fluidity of the composition as well as heat resistance, moisture absorption resistance, flame retardancy, etc. of a cured product, a bisphenol A epoxy resin, a tetramethylbiphenol epoxy resin except for epoxy resin (1), a, 4,4'-biphenol epoxy resin, a biphenyl aralkyl epoxy resin, a phenol aralkyl epoxy resin, a dihydroxyanthracene epoxy resin, a dicyclopentadiene epoxy resin, an ortho-cresol novolak epoxy resin, and a trisphenolmethane-type epoxy resin are particularly preferred.

In the case where the epoxy resin composition of the present invention contains the other epoxy resin above, the content thereof is preferably from 0.01 to 60 parts by weight, more preferably 40 parts by weight or less, still more preferably 30 parts by weight or less, and yet still more preferably 20 parts by weight or less, per 100 parts by weight of the entire epoxy resin components in the composition, and on the other hand, the content is preferably 1 part by weight or more.

[Curing Accelerator]

The epoxy resin composition of the present invention preferably contains a curing accelerator. When a curing accelerator is contained, it becomes possible to shorten the curing time, lower the curing temperature and in turn, facilitate obtaining a desired cured product.

The curing accelerator is not particularly limited, and specific examples thereof include a phosphorus compound such as organic phosphines and phosphonium salt, a tetraphenylboronate, an organic acid dihydrazide, and a halogenated boron amine complex.

Examples of the phosphorus compound usable as the curing accelerator include organic phosphines such as triphenylphosphine, diphenyl(p-tolyl)phosphine, tris(alkylphenyl)phosphine, tris(alkoxyphenyl)phosphine, tris(alkylalkoxyphenyl)phosphine, tris(dialkylphenyl)phosphine, tris(trialkylphenyl)phosphine, tris(tetraalkylphenyl)phosphine, tris(dialkoxyphenyl)phosphine, tris(trialkoxyphenyl)phosphine, tris(tetraalkoxyphenyl)phosphine, trialkylphosphine, dialkylarylphosphine and alkyldiarylphosphine; a complex of organic phosphines above and organoborons; and a compound obtained by adding to the organic phosphines above a maleic anhydride, a quinone compound such as 1,4-benzoquinone, 2,5-toluquinone, 1,4-naphthoquinone, 2,3-dimethylbenzoquinone, 2,6-dimethylbenzoquinone, 2,3-dimethoxy-5-methyl-1,4-benzoquinone, 2,3-dimethoxy-1,4-benzoquinone and phenyl-1,4-benzoquinone, or a compound such as diazophenylmethane.

Among the curing accelerators recited above, organic phosphines and a phosphonium salt are preferred, and organic phosphines are most preferred. As the curing accelerator, only one of those recited above may be used, or two or more thereof may be mixed and used in any combination in an arbitrary ratio.

The curing accelerator is preferably used in an amount ranging from 0.1 to 20 parts by weight per 100 parts by weight of the entire epoxy resin components in the epoxy resin composition. The content is more preferably 0.5 parts by weight or more, and still more preferably 1 part by weight or more, and on the other hand, is more preferably 15 parts by weight or less, and still more preferably 10 parts by weight or less. When the content of the curing accelerator is not less than the lower limit value above, a good curing acceleration effect can be obtained, whereas when the content is not more than the upper limit value above, it is advantageously easy to obtain desired curing physical properties.

[Inorganic Filler]

In the epoxy resin composition of the present invention, an inorganic filler can be blended. The inorganic filler includes, for example, fused silica, crystalline silica, glass powder, alumina, calcium carbonate, calcium sulfate, talc, and boron nitride. Only one of these may be used, or two or more thereof may be combined and used in any combination in an arbitrary blending ratio. Among these, in the case of using the composition for semiconductor sealing, a fused and/or crystalline silica powder filler of crushed type and/or spherical form is preferred.

When the inorganic filler is used, in the case of using the epoxy resin as a semiconductor sealing material, the coefficient of thermal expansion of the semiconductor sealing material can be made close to that of an internal silicon chip or lead frame and in addition, the moisture absorption of the semiconductor sealing material as a whole can be reduced, so that solder crack resistance can be enhanced.

The average particle diameter of the inorganic filler is usually from 1 to 50 μm, preferably from 1.5 to 40 μm, and more preferably from 2 to 30 μm. The average particle diameter is preferably not less than the lower limit value above for the reason that the melt viscosity does not become excessively high and the fluidity is less likely to lower, and the average particle diameter is preferably not more than the upper limit value above, since the filler hardly causes clogging in a narrow gap of a die at the time of molding and the filling property of a material is likely to be enhanced.

In the case of using an inorganic filler in the epoxy resin composition of the present invention, the inorganic filler is preferably blended in the range of 60 to 95 wt % of the epoxy resin composition as a whole.

[Release Agent]

In the epoxy resin composition of the present invention, a release agent can be blended. As the release agent, for example, a natural wax such as carnauba wax, a synthetic wax such as polyethylene wax, higher fatty acids such as stearic acid zinc stearate, metal salts thereof, and a hydrocarbon release agent such as paraffin, can be used. Only one of these may be used, or two or more thereof may be combined and used in any combination in an arbitrary blending ratio.

In the case of blending a release agent in the epoxy resin composition of the present invention, the blending amount of the release agent is preferably from 0.1 to 5.0 parts by weight, more preferably from 0.5 to 3.0 parts by weight, per 100 parts by weight of the entire epoxy resin component in the epoxy resin composition. The blending amount of the release agent is preferably within the range above, since a good releasing property can be exhibited with maintaining the curing properties of the epoxy resin composition.

[Coupling Agent]

In the epoxy resin composition of the present invention, a coupling agent is preferably blended. The coupling agent is preferably used in combination with an inorganic filler, and when a coupling agent is blended, the adhesiveness of the epoxy resin as a matrix to the inorganic filler can be enhanced. The coupling agent includes a silane coupling agent, a titanate coupling agent, etc.

The silane coupling agent includes, for example, an epoxy silane such as γ-glycidoxypropyltrimethoxysilane, γ-glycidoxypropyltriethoxysilane and β-(3,4-epoxycyclohexyl)ethyltrimethoxysilane; an aminosilane such as γ-aminopropyltriethoxysilane, N-β(aminoethyl)γ-aminopropyltrimethoxysilane, N-β(aminoethyl)γ-aminopropylmethyldimethoxysilane, γ-aminopropyltrimethoxysilane and γ-ureidopropyltriethoxysilane; a mercaptosilane such as 3-mercaptopropyltrimethoxysilane; a vinyl silane such as p-styryltrimethoxysilane, vinyltrichlorosilane, vinyltris(β-methoxyethoxy)silane, vinyltrimethoxysilane, vinyltriethoxysilane and γ-methacryloxypropyltrimethoxysilane; and epoxy-based, amino-based and vinyl-based silanes of a high molecular type.

The titanate coupling agent includes, for example, isopropyltriisostearoyl titanate, isopropyltri(N-aminoethyl-.aminoethyl) titanate, diisopropylbis(dioctylphosphate)titanate, tetraisopropylbis(dioctylphosphite)titanate, tetraoctylbis(ditridecylphosphite)titanate, tetra(2,2-diallyloxymethyl-1-butyl)bis(ditridecyl)phosphite titanate, bis(dioctylpyrophosphate)oxyacetate titanate, and bis(dioctylpyrophosphate)ethylene titanate.

As to all of these coupling agents, only one may be used, or two or more may be mixed and used in any combination in an arbitrary ratio.

In the case of using a coupling agent in the epoxy resin composition of the present invention, the blending amount thereof is preferably from 0.1 to 3.0 parts by weight per 100 parts by weight of the entire epoxy resin components. The blending amount of the coupling agent is preferably not less than the lower limit value above for the reason that the effect of increasing the adhesiveness of the epoxy resin as a matrix to the inorganic filler due to blending of the coupling agent tends to be enhanced, and on the other hand, the blending amount of the coupling agent is preferably not more than the upper limit value above, since the coupling agent is less likely to bleed out from the obtained cured product.

[Other Component]

In the epoxy resin composition of the present invention, a component other than those described above (in the present invention, the component is sometimes referred to as "other component") may be blended. The other component includes, for example, a flame retardant, a plasticizer, a reactive diluent, and a pigment, and this can be appropriately blended as needed. However, it is not excluded to blend a component other than the components described above in the epoxy resin composition of the present invention.

The flame retardant for use in the epoxy resin composition of the present invention includes, for example, a halogen flame retardant such as brominated epoxy resin and brominated phenol resin, an antimony compound such as antimony trioxide, a phosphorus flame retardant such as red phosphorus, phosphoric acid esters and phosphines, a nitrogen flame retardant such as melamine derivative, and an inorganic flame retardant such as aluminum hydroxide and magnesium hydroxide.

[Cured Product]

The cured product of the present invention can be obtained by curing the epoxy resin composition of the present invention. The cured product of the present invention obtained by curing the epoxy resin composition of the present invention has excellent properties in terms of heat resistance and moisture absorption resistance, particularly in terms of heat resistance.

Although the method for curing the epoxy resin composition of the present invention is not particularly limited, usually, the cured product can be obtained by a thermosetting reaction by heating. At the time of thermosetting reaction, it is preferable to appropriately select the curing temperature according to the kind of the curing agent used. For example, in the case of using a phenolic curing agent, the curing temperature is usually from 130 to 300° C. In addition, the curing temperature can be lowered by adding a curing accelerator to the curing agent. The reaction time is preferably from 1 to 20 hours, more preferably from 2 to 18 hours, and still more preferably from 3 to 15 hours. The reaction time is preferably not less than the lower limit value above, since the curing reaction tends to sufficiently proceed with ease. On the other hand, the reaction time is preferably not more than the upper limit value above for the reason that deterioration due to heating and an energy loss during heating are readily reduced.

The epoxy resin composition of the present invention can provide a cured product having excellent heat resistance and preferably having a glass transition temperature (Tg) of 115° C. or more. The glass transition temperature of the cured product is preferably higher, since in the case of use as a semiconductor sealing material, etc., a thermal stress is hardly generated in the resin sealed and damage to passivation or chip or failure such as sliding and package cracking of aluminum wiring is less likely to occur.

Here, the glass transition temperature (Tg) is measured by the method described in Examples later.

In addition, the epoxy resin composition of the present invention has excellent heat resistance and exhibits a low modulus of elasticity in high temperature, and the modulus is 10 MPa or less. The modulus of elasticity is preferably lower at a high temperature, since in the case of use as a semiconductor sealing material, etc., a thermal stress is hardly generated in the resin sealed and damage to passivation or chip or failure such as sliding and package cracking of aluminum wiring is less likely to occur.

Here, the modulus of elasticity in high temperature is measured by the method described in Examples later.

[Use]

Epoxy resin (1) of the present invention has a low hydrolyzable chlorine amount and excellent solvent solubility, and the epoxy resin composition of the present invention containing epoxy resin (1) of the present invention is excellent in heat resistance, etc. Accordingly, these can be effectively used for any application as long as it is an application requiring these physical properties. For example, the epoxy resin and epoxy resin composition of the present invention can be suitably used for any application in the fields including: paints such as electrodeposition paint for automobiles, heavy duty paint for vessels and bridges and paint for internal coating of beverage can; electrics and electronics such as laminate sheet, semiconductor sealing material, insulating powdery paint and coil impregnation; civil engineering, constructions and adhesives in seismic strengthening of bridges, concrete reinforcement, flooring of buildings, lining of water utilities, drainage and water permeation pavement, and adhesive for vehicles and aircrafts; etc. Among these, the epoxy resin and epoxy resin composition of the present invention are useful particularly for electric and electronic applications such as semiconductor sealing material and laminate sheet.

The epoxy resin composition of the present invention may be cured and then used for the above-described application or may be cured in the manufacturing process of the above-described application.

EXAMPLES

Although the present invention is described more specifically below based on Examples, the present invention is by no means limited by the following Examples. In the following Examples, the values for various production conditions or evaluation results have a meaning as a preferable value of the upper or lower limit in the embodiments of the present invention, and the preferable range may be a range defined by a combination of the above-described upper or lower limit value and the value in the following Examples or a combination of values in Examples.

Production and Evaluation 1 of Epoxy Resin

Production Example 1-1

Into a four-necked flask having an inner volume of 2 L and equipped with a thermometer, a stirrer, and a cooling tube, 137 g of tetramethylbiphenol (2) (produced by Mitsubishi Chemical Corporation), 627 g of epichlorohydrin, 244 g of isopropyl alcohol, and 87 g of water were charged. The contents were uniformly dissolved by raising the temperature to 65° C., and 108 g of an aqueous 48.5 wt % sodium hydroxide solution was then added dropwise over 90 minutes. After the completion of dropwise addition, the system was held at 65° C. for 30 minutes to complete the reaction, and the reaction solution was transferred into a 3 L separating funnel and allowed to stand still in a state at 65° C. for one hour. Thereafter, water layer was extracted from separated oil layer and water layer, thereby removing a byproduct salt and excess sodium hydroxide. Subsequently, excess epichlorohydrin and isopropyl alcohol were removed from the product by distillation under reduced pressure to obtain a crude epoxy resin.

This crude epoxy resin was dissolved in 300 g of methyl isobutyl ketone and after adding 4 g of an aqueous 48.5 wt % sodium hydroxide solution, the reaction was again allowed to proceed at a temperature of 65° C. for one hour. After that, 167 g of methyl isobutyl ketone was added, and the solution was washed with water four times by using 500 g of water. Subsequently, methyl isobutyl ketone was completely removed under reduced pressure at 150° C. to obtain an epoxy resin having an epoxy equivalent of 185 g/eq.

Production Example 1-2

Into a four-necked flask having an inner volume of 2 L and equipped with a thermometer, a stirrer, and a cooling tube, 0.5 mol of tetramethylbiphenol (2) (produced by Mitsubishi Chemical Corporation), 4 mol of epichlorohydrin, and tetramethylammonium chloride in an amount of 2 times by weight that of tetramethylbiphenol (2) were charged. The reaction was performed under the same reaction conditions as in Example 1 of Patent Document 1, and epichlorohydrin was recovered in the same manner. Thereafter, 500 ml of toluene was added, and the solution was washed with water three times by using 1 L of water. Toluene was then removed under reduced pressure to obtain an epoxy resin having an epoxy equivalent of 202 g/eq.

Example 1-1

Into a four-necked flask having an inner volume of 2 L and equipped with a thermometer, a stirrer, and a cooling tube, 100 g of the epoxy resin obtained in Production Example 1-1, 120 g of methyl isobutyl ketone, and 30 g of dimethylsulfoxide were charged. The contents were uniformly dissolved by raising the reaction temperature to 65° C., and 9.7 g of a 8 wt % potassium hydroxide/isopropanol solution was then added. After allowing the reaction to proceed for one hour, 112 g of methyl isobutyl ketone was added, and the solution was washed with water four times by using 200 g of water. Subsequently, methyl isobutyl ketone was completely removed under reduced pressure at 150° C. to obtain an epoxy resin.

Example 1-2

An epoxy resin was obtained by the same method as in Example 1-1 except that the 8 wt % potassium hydroxide/isopropanol solution was added in an amount of 8.7 g and the reaction temperature was changed to 60° C.

Example 1-3

An epoxy resin was obtained by the same method as in Example 1-1 except that the 8 wt % potassium hydroxide/isopropanol solution was added in an amount of 10.7 g and the reaction temperature was changed to 80° C.

Example 1-4

Into a four-necked flask having an inner volume of 2 L and equipped with a thermometer, a stirrer, and a cooling tube, 100 g of the epoxy resin obtained in Production Example 1-1, 80 g of methyl isobutyl ketone, and 20 g of dimethylsulfoxide were charged. The contents were uniformly dissolved by raising the reaction temperature to 65° C., and 2.0 g of a 8 wt % potassium hydroxide/isopropanol solution was then added. After allowing the reaction to proceed for one hour, 162 g of methyl isobutyl ketone was added, and the solution was washed with water four times by using 200 g of water. Subsequently, methyl isobutyl ketone was completely removed under reduced pressure at 150° C. to obtain an epoxy resin.

Comparative Example 1-1

The epoxy resin synthesized in Production Example 1-1 was used.

Comparative Example 1-2

An epoxy resin was obtained by the same method as in Example 1-1 except that the amount of the 8 wt % potassium hydroxide/isopropanol solution added was changed to 2.4 g.

Comparative Example 1-3

An epoxy resin was obtained by the same method as in Example 1-1 except that the 8 wt % potassium hydroxide/isopropanol solution was added in an amount of 15.0 g and the reaction temperature was changed to 80° C.

Comparative Example 1-4

The epoxy resin synthesized in Production Example 1-2 was used.

Comparative Example 1-5

Into a four-necked flask having an inner volume of 2 L and equipped with a thermometer, a stirrer, and a cooling tube, 100 g of the epoxy resin obtained in Production Example 1-1, 80 g of methyl isobutyl ketone, and 20 g of dimethylsulfoxide were charged. The contents were uniformly dissolved by raising the reaction temperature to 65° C., and 2.4 g of an aqueous 48 wt % sodium hydroxide solution was then added. After allowing the reaction to proceed for one hour, 162 g of methyl isobutyl ketone was added, and the solution was washed with water four times by using 200 g of water. Subsequently, methyl isobutyl ketone was completely removed under reduced pressure at 150° C. to obtain an epoxy resin.

The epoxy resins obtained in Examples 1-1 to 1-4 and Comparative Examples 1-1 to 1-5 were measured for epoxy equivalent, hydrolyzable chlorine amount, melt viscosity at 150° C., weight average molecular weight (Mw), and number average molecular weight (Mn) by the methods described above and at the same time, subjected to the following solvent solubility test. The results are shown in Table 1.

[Solvent Solubility Test]

Using toluene, methyl ethyl ketone (MEK), methyl isobutyl ketone (MIBK) or acetone as the test solvent, a test solution was prepared by adding the epoxy resin to each solvent to afford a predetermined resin concentration (40 wt % or 20 wt %), and 20 ml of test solution was weighed into a 50 ml vial. Thereafter, the epoxy resin was completely dissolved by heating and stored at a predetermined temperature (23° C. or 5° C.), and the solvent solubility was rated as good "A" when a crystal was not precipitated within one month, rated as "B" when a crystal was precipitated at less than 25 wt %, and rated as "C" when a crystal was precipitated at 25 wt % or more.

TABLE 1

| | | | Example | | | | Comparative Example | | | | |
|---|---|---|---|---|---|---|---|---|---|---|---|
| | | Unit | 1-1 | 1-2 | 1-3 | 1-4 | 1-1 | 1-2 | 1-3 | 1-4 | 1-5 |
| Physical properties of epoxy resin | Epoxy equivalent | g/eq | 209 | 200 | 255 | 198 | 185 | 194 | 280 | 202 | 198 |
| | hydrolyzable chlorine amount | ppm | 50 | 80 | 10 | 100 | 500 | 100 | <10 | 9020 | 450 |
| | Melt viscosity (150° C.) | Pa·s | 0.1 | 0.1 | 1.4 | 0.1 | 0.1 | 0.1 | 4 | 0.1 | 0.1 |
| | Weight average molecular weight (Mw) | — | 615 | 445 | 2675 | 418 | 274 | 364 | 6084 | 320 | 431 |
| | Number average molecular weight (Mn) | — | 304 | 281 | 411 | 277 | 242 | 268 | 470 | 255 | 279 |
| | Solvent | resin content (%) | | | | | | | | | |
| Solvent solubility, test results | Toluene (23° C.) | 40 | A | A | A | C | C | C | A | C | C |
| | MEK (23° C.) | 40 | A | A | A | B | C | C | A | C | C |
| | MIBK (5° C.) | 20 | A | A | A | B | C | C | A | C | C |
| | Acetone (5° C.) | 40 | A | A | A | B | C | C | A | C | C |

Production and Evaluation 1 of Epoxy Resin Composition

Examples 1-5 to 1-7 and Comparative Examples 1-6 to 1-8

An epoxy resin and a curing agent were blended in a ratio shown in Table 2, stirred with heating to 100° C. until becoming uniform, and then cooled to 80° C., and a curing accelerator was added in a ratio shown in Table 2. The mixture was stirred until becoming uniform to prepare an epoxy resin composition. In Table 2, "parts" indicates "parts by weight".

The curing agent and curing accelerator used are as follows.

Curing agent: A phenol aralkyl resin (produced by Meiwa Plastic Industries, Ltd., trade name: MEH7800 (hydroxyl equivalent: 174 g/eq))

Curing accelerator: Triphenylphosphine (produced by Tokyo Chemical Industry Co., Ltd., trade name: Triphenylphosphine)

Two glass plates each having a release PET film laminated to one surface were prepared, and a casting plate was manufactured by arranging the release PET film sides of these glass plates to serve as inner surfaces and adjusting the distance between glass plates to be 4 mm.

The epoxy resin composition was cast into the casting plate and cured by heating at 120° C. for 2 hours, then at 175° C. for 6 hours, to obtain a cured product.

With respect to the obtained cured products, as the evaluation of heat resistance, the glass transition temperature was measured by the following method, and the results are shown in Table 2.

[Measurement of Glass Transition Temperature (Tg(E"))]

A test piece was obtained by cutting the cured product into 5 cm height, 1 cm width, and 4 mm thickness. Analysis was performed by the following measurement method in a three-point bend mode by means of a thermal mechanical analyzer (DMS: manufactured by Seiko Instruments, Inc., EXSTAR 6100), and the peak top of E" at 1 Hz was defined as Tg(E").

(Measurement Method)

First temperature rise: 5° C./min, from 30° C. up to 250° C.

TABLE 2

|  |  |  | Example | | | Comparative Example | | |
|---|---|---|---|---|---|---|---|---|
|  |  |  | 1-5 | 1-6 | 1-7 | 1-6 | 1-7 | 1-8 |
| Blending of epoxy resin composition | Epoxy resin of Example 1-1 | parts | 100 |  |  |  |  |  |
|  | Epoxy resin of Example 1-2 | parts |  | 100 |  |  |  |  |
|  | Epoxy resin of Example 1-3 | parts |  |  | 100 |  |  |  |
|  | Epoxy resin of Comparative Example 1-1 | parts |  |  |  | 100 |  |  |
|  | Epoxy resin of Comparative Example 1-2 | parts |  |  |  |  | 100 |  |
|  | Epoxy resin of Comparative Example 1-3 | parts |  |  |  |  |  | 100 |
|  | Curing agent | parts | 83 | 87 | 68 | 94 | 90 | 62 |
|  | Curing accelerator | parts | 1 | 1 | 1 | 1 | 1 | 1 |
|  | Tg (E") | ° C. | 120 | 120 | 115 | 119 | 121 | 98 |

[Evaluation 1 of Results]

It is seen from Table 1 that all of the epoxy resins of Examples 1-1 to 1-4 have excellent solvent solubility compared to the epoxy resins of Comparative Examples 1-1, 1-2, 1-4 and 1-5.

In addition, it is seen from Table 2 that the epoxy resin cured products of Examples 1-5 to 1-7 have heat resistance comparable to that of the epoxy resin cured products of Comparative Examples 1-6 and 1-7 and have more excellent heat resistance than that of the epoxy resin cured product of Comparative Example 1-8.

Production and Evaluation 2 of Epoxy Resin

Production Example 2-1

Into a four-necked flask having an inner volume of 2 L and equipped with a thermometer, a stirrer, and a cooling tube, 137 g of tetramethylbiphenol (produced by Mitsubishi Chemical Corporation), 627 g of epichlorohydrin, 244 g of isopropyl alcohol, and 87 g of water were charged. The contents were uniformly dissolved by raising the temperature to 65° C., and 108 g of an aqueous 48.5 wt % sodium hydroxide solution was then added dropwise over 90 minutes. After the completion of dropwise addition, the system was held at 65° C. for 30 minutes to complete the reaction, and the reaction solution was transferred into a 3 L separating funnel and allowed to stand still in a state at 65° C. for one hour. Thereafter, water layer was extracted from separated oil layer and water layer, thereby removing a byproduct salt and excess sodium hydroxide. Subsequently, excess epichlorohydrin and isopropyl alcohol were removed from the product by distillation under reduced pressure to obtain a crude epoxy resin.

This crude epoxy resin was dissolved in 300 g of methyl isobutyl ketone and after adding 4 g of an aqueous 48.5 wt % sodium hydroxide solution, the reaction was again allowed to proceed at a temperature of 65° C. for one hour. After that, 167 g of methyl isobutyl ketone was added, and the solution was washed with water four times by using 500 g of water. Subsequently, methyl isobutyl ketone was completely removed under reduced pressure at 150° C. to obtain an epoxy resin having an epoxy equivalent of 185 g/eq.

Example 2-1

Into a four-necked flask having an inner volume of 2 L and equipped with a thermometer, a stirrer, and a cooling tube, 100 g of the epoxy resin obtained in Production Example 2-1, 120 g of methyl isobutyl ketone, and 30 g of dimethylsulfoxide were charged. The contents were uniformly dissolved by raising the reaction temperature to 65° C., and 4.8 g of a 8 wt % potassium hydroxide/isopropanol solution was then added. After allowing the reaction to proceed for one hour, 112 g of methyl isobutyl ketone was added, and the solution was washed with water four times by using 200 g of water. Subsequently, methyl isobutyl ketone was completely removed under reduced pressure at 150° C. to obtain an epoxy resin.

Example 2-2

An epoxy resin was obtained by the same method as in Example 2-1 except that the amount of the 8 wt % potassium hydroxide/isopropanol solution added was changed to 7.1 g.

Comparative Example 2-1

The epoxy resin synthesized in Production Example 2-1 was used.

Comparative Example 2-2

An epoxy resin was obtained by the same method as in Example 2-1 except that the amount of the 8 wt % potassium hydroxide/isopropanol solution added was changed to 2.4 g.

Comparative Example 2-3

An epoxy resin was obtained by the same method as in Example 2-1 except that the amount of the 8 wt % potassium hydroxide/isopropanol solution added was changed to 9.7 g.

The epoxy resins obtained in Examples 2-1 and 2-2 and Comparative Examples 2-1 to 2-3 were measured for epoxy equivalent, hydrolyzable chlorine amount, melt viscosity at 150° C., weight average molecular weight (Mw), and number average molecular weight (Mn) by the methods described above and at the same time, subjected to the following crystallization test. The results are shown in Table 3.

[Crystallization Test]

After weighing 20 g of epoxy resin into a 50 cc vial, the epoxy resin was completely dissolved by heating at 150° C. and stored at 23° C. The crystallization rate was rated as good "A" when the resin was fully crystallized in the vial within 7 hours, and the crystallization rate was rated as "C" when the resin was not crystallized.

TABLE 3

|  |  |  | Example | | Comparative Example | | |
|---|---|---|---|---|---|---|---|
|  |  | Unit | 2-1 | 2-2 | 2-1 | 2-2 | 2-3 |
| Physical properties of epoxy resin | Epoxy equivalent | g/eq | 196 | 199 | 185 | 194 | 209 |
|  | Hydrolyzable chlorine amount | ppm | 80 | 70 | 500 | 100 | 50 |
|  | Melt viscosity (150° C.) | Pa · s | 0.1 | 0.1 | 0.1 | 0.1 | 0.1 |
|  | Weight average molecular weight (Mw) | — | 391 | 431 | 274 | 364 | 615 |
|  | Number average molecular weight (Mn) | — | 271 | 278 | 242 | 268 | 304 |
|  | Crystallization test |  | A | A | C | C | C |

[Production and Evaluation 2 of Epoxy Resin Composition]

Examples 2-3 and 2-4 and Comparative Examples 2-4 and 2-5

An epoxy resin and a curing agent were blended in a ratio shown in Table 4, stirred with heating to 100° C. until becoming uniform, and then cooled to 80° C., and a curing accelerator was added in a ratio shown in Table 4. The mixture was stirred until becoming uniform to prepare an epoxy resin composition. In Table 4, "parts" indicates "parts by weight".

The curing agent and curing accelerator used are as follows.

Curing agent: A phenol aralkyl resin (produced by Meiwa Plastic Industries, Ltd., trade name: MEH7800 (hydroxyl equivalent: 174 g/eq))

Curing accelerator: Triphenylphosphine (produced by Tokyo Chemical Industry Co., Ltd., trade name: Triphenylphosphine)

Two glass plates each having a release PET film laminated to one surface were prepared, and a casting plate was manufactured by arranging the release PET film sides of these glass plates to serve as inner surfaces and adjusting the distance between glass plates to be 4 mm.

The epoxy resin composition was cast into the casting plate and cured by heating at 120° C. for 2 hours, then at 175° C. for 6 hours to obtain a cured product.

With respect to the obtained cured products, as the evaluation of heat resistance, the modulus of elasticity in high temperature was measured by the following method, and the results are shown in Table 4.

[Measurement of Modulus of Elasticity (200° C. (E')) at High Temperatures]

A test piece was obtained by cutting the cured product into 5 cm height, 1 cm width, and 4 mm thickness. Analysis was performed by the following measurement method in a three-point bend mode by means of a thermal mechanical analyzer (DMS: manufactured by Seiko Instruments, Inc., EXSTAR 6100), and 200° C. (E') at 1 Hz was defined as the modulus of elasticity in high temperature.

(Measurement Method)

First temperature rise: 5° C./min, from 30° C. up to 250° C.

TABLE 4

|  |  |  | Example | | Comparative Example | |
|---|---|---|---|---|---|---|
|  |  |  | 2-3 | 2-4 | 2-4 | 2-5 |
| Blending of epoxy resin composition | Epoxy resin of Example 2-1 | parts | 100 |  |  |  |
|  | Epoxy resin of Example 2-2 | parts |  | 100 |  |  |
|  | Epoxy resin of Comparative Example 2-1 | parts |  |  | 100 |  |
|  | Epoxy resin of Comparative Example 2-2 | parts |  |  |  | 100 |
|  | Curing agent | parts | 89 | 87 | 93 | 90 |
|  | Curing accelerator | parts | 1 | 1 | 1 | 1 |
|  | Modulus (E') of elasticity at 200° C. | MPa | 10 | 10 | 12 | 12 |

[Evaluation 2 of Results]

It is seen from Table 3 that both of the epoxy resins of Examples 2-1 and 2-2 have an excellent crystallization rate compared to the epoxy resins of Comparative Examples 2-1 to 2-3.

In addition, it is seen from Table 4 that the epoxy resin cured products of Examples 2-3 and 2-4 have more excellent low modulus of elasticity than that of the epoxy resin cured products of Comparative Examples 2-4 and 2-5.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2015-173911) filed on Sep. 3, 2015 and Japanese Patent Application (Patent Application No. 2015-174043) filed on Sep. 3, 2015, the contents of which are incorporated herein by way of reference.

The invention claimed is:

1. An epoxy resin represented by the following formula (1), having a number average molecular weight (Mn) of 270 to 460, a weight average molecular weight (Mw) of 418 to 2,675, an epoxy equivalent from 196 to 255 g/eq, and a content of hydrolysable chlorine of 90 ppm or less relative to the epoxy resin:

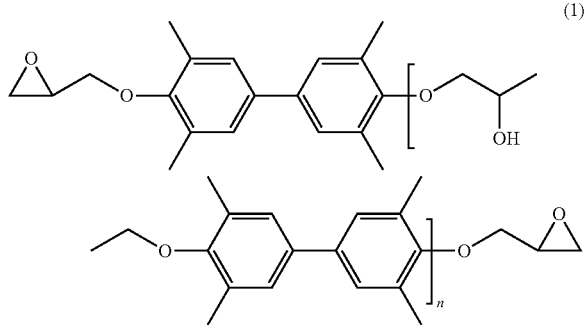

wherein, n represents an integer of 0 to 10.

2. The epoxy resin according to claim 1, wherein the melt viscosity at 150° C. is 3.0 Pa s or less.

3. An epoxy resin composition comprising from 0.1 to 1,000 parts by weight of a curing agent per 100 parts by weight of the epoxy resin according to claim 1.

4. The epoxy resin composition according to claim 3, wherein the curing agent is at least one curing agent selected from the group consisting of a phenolic curing agent, an amine curing agent, an acid anhydride curing agent, and an amide curing agent.

5. The epoxy resin composition according to claim 3, further comprising an epoxy resin different from the epoxy resin according to claim 1.

6. The epoxy resin composition according to claim 5, wherein the epoxy resin is produced by the steps of:

reacting a raw material solution containing epichlorohydrin, tetramethylbiphenol and another polyvalent hydroxy compound with an alkali metal hydroxide at 80-100° C. to obtain a crude epoxy resin, and reacting the crude epoxy resin with a strong alkali to purify the crude epoxy resin.

7. The epoxy resin composition according to claim 6, wherein an amount of the alkali metal hydroxide used in the reaction is in a rage of 0.9 to 1.6 equivalents, per equivalent of the hydroxyl group in an entire polyhydric hydroxy compound, said entire polyhydric hydroxy compound being the total of the tetramethylbiphenol and the other polyvalent hydroxy compound.

8. A cured product obtained by curing the epoxy resin composition according to claim 3.

9. An electric or electronic component obtained by curing the epoxy resin composition according to claim 3.

* * * * *